United States Patent
Burnett et al.

(12)

(10) Patent No.: US 6,303,751 B1
(45) Date of Patent: Oct. 16, 2001

(54) HUMAN METABOTROPIC GLUTAMATE RECEPTOR AND RELATED DNA COMPOUNDS

(75) Inventors: J. Paul Burnett; Nancy G. Mayne; Robert L. Sharp; Yvonne M. Snyder, all of Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 960 days.

(21) Appl. No.: 08/538,526

(22) Filed: Oct. 3, 1995

Related U.S. Application Data

(62) Division of application No. 08/097,497, filed on Jul. 23, 1993, now abandoned, which is a division of application No. 07/884,571, filed on May 8, 1992, now abandoned.

(51) Int. Cl.$^7$ ............................ C12N 15/12; C07K 14/705
(52) U.S. Cl. ............................ 530/350; 530/395; 536/23.5
(58) Field of Search .................................. 530/350, 395; 536/23.5

(56) References Cited

U.S. PATENT DOCUMENTS 5,385,831 * 1/1995 Mulvihill et al. .................... 435/69.1

FOREIGN PATENT DOCUMENTS

WO 92/10583   6/1992   (WO) ............................ C12P/21/06
WO 94/29449  12/1994   (WO) ............................ C12N/15/12

OTHER PUBLICATIONS

D.K. Grandy et al. "Cloning of the cDNA and Gene for a Human D2 Dopamine Receptor", Proc. Natl. Acad. Sci. 86: 9762–9766, Dec. 1989.*

N.P. Gerard et al., The Human Neurokinin A (Substance K) Receptor, J. Biol. Chem. 265(33): 20455–20462, Nov. 1990.*

Q.Y. Zhou et al., "Cloning and Expression of Human and Rat D1 Dopamine Receptors", Nature 347: 76–80, Sep. 1990.*

Tanabe, Masu, Ishii, Shigemoto, and Nakanishi, "A Family Metabotropic Glutamate Receptors," *Neuron*, 8, 169–179 (1992).

Masu, Tanabe, Tsuchida, Shigemoto, and Nakanishi, "Sequence and Expression of a Metabotropic Glutamate Receptor," *Nature*, 349, 760–765 (1991).

Houamed, Kuijper, Gilbert, Haldeman, O'Hara, Malvihill Almers, and Hagen, "Cloning, Expression, and Gene Structure of a G Protein–Coupled Glutamate Receptor from Rat Brain," *Science*, 252, 1318–1321 (1991).

Aramori and Nakanishi, "Signal Transduction and Pharmacological Characteristics of a Metabotropic Glutamate Receptor, mGluR1, in Transfected CHO Cells," *Neuron*, 8, 757–765 (1992).

S.C. Berger, et al., "Guide to Molecular Cloning Techniques", *Meth. in Enzymology*, vol. 152:393–399, 415–423, 432–447, 661–704 (1987).

* cited by examiner

Primary Examiner—Rebecca E. Prouty
(74) Attorney, Agent, or Firm—Alexander Wilson; Thomas D. Webster

(57) ABSTRACT

This invention provides a human glutamate receptor and functional equivalents thereof, and nucleic acids compounds which encode the receptor. The invention also provides assays, probes and primers, and other molecular biology techniques which utilize the compounds disclosed.

1 Claim, No Drawings

HUMAN METABOTROPIC GLUTAMATE RECEPTOR AND RELATED DNA COMPOUNDS

This application is a division, of application Ser. No. 08/097,497 filed Jul. 23, 1993 now abandoned which is a division of application Ser. No. 07/884,571 filed May 8, 1992 now abandoned.

BACKGROUND OF THE INVENTION

In the mammalian central nervous system, L-glutamate serves as a major excitatory neurotransmitter. The interaction of glutamate with its membrane bound receptors is believed to play a role in many important neuronal processes including fast synaptic transmission, synaptic plasticity and long-term potentiation. These processes are fundamental to the maintenance of life and normal human abilities such as learning and memory. Monaghan, D. T. et al., 8 Neuron 267 (1992).

Pharmacological characterization of receptors for L-glutamate has led to their classification into two families based on their biological function: the ionotropic receptors which are directly coupled to cation channels in the cell membrane, and the metabotropic receptors which function through coupling to G-proteins. The present invention concerns a member of the metabotropic family of glutamate receptors.

In addition to its role in normal human physiology, interaction of L-glutamate with its receptors is believed to play a key role in many neurological disorders such as stroke, epilepsy and head trauma, as well as neurodegenerative processes such as Alzheimer's disease. Olney, R. W., 17 *Drug Dev. Res.* 299 (1989). For this reason, understanding the molecular structure of human L-glutamate receptors is important for understanding these disease processes as well as for searching for effective therapeutic agents. Up to the present, the search for therapeutic agents which will bind and modulate the function of human glutamate receptors has been hampered by the unavailability of homo-geneous sources of receptors. The brain tissues commonly used by pharmacologists are derived from experimental animals (non-human) and furthermore contain mixtures of various types of glutamate receptors.

Moreover, in searching for drugs for human therapy, it is obviously desirable to use receptors which are more analogous to those in the intact human brain than are the rodent receptors employed to date. The current invention provides a human receptor which can be used to search selectively for drugs which modulate these receptors.

Recently, four metabotropic receptor subtypes (mGluR1-mGluR4) have been cloned from rat brain. Masu et al., 349 Nature 760 (1991), Houamed et al., 252 Science 1314 (1991) and Tanabe Y. et al. 8 Neuron 169 (1991). In addition, two alternately spliced versions of mGluR1 are known. Tanabe Y. et al. 8 Neuron 169 (1991).

The present invention provides a functional human metabotropic glutamate receptor to the common store of knowledge. The new receptor, called HSmGluR1, will prove especially beneficial to the development of human therapeutic agents.

SUMMARY OF THE INVENTION

The present invention provides compounds which comprise the amino acid sequence SEQ ID NO:1. In particular, the amino acid compound which is SEQ ID NO:1 is preferred.

The invention also provides nucleic acid compounds which comprise a nucleic acid sequence which encodes the amino acid compounds provided. Particularly, nucleic acid compounds which are DNA are preferred. Most preferred is the DNA compound SEQ ID NO:2. However, also preferred are those nucleic acid compounds which are sense mRNA.

Also provided by the present invention are recombinant nucleic acid vectors comprising the nucleic acids which encode SEQ ID NO:1. The preferred nucleic acid vectors are those which are DNA. Most preferred are recombinant DNA vectors which comprise the DNA sequence which is SEQ ID NO:2. A preferred DNA vector which comprises SEQ ID NO:2 is pRS117.

Moreover, recombinant DNA vectors of the present invention preferably comprise a promoter positioned to drive expression of a DNA sequence which encodes SEQ ID NO:1. Those vectors wherein said promoter functions in mammalian cells are preferred. Those mammalian vectors wherein said promoter functions in AV12 cells are preferred. The recombinant DNA expression vector most preferred is plasmid pRS121.

Restriction fragments of the preferred vectors are also provided. Particularly, the approximately 4.1 kb EcoRI and the approximately 3.8 kb BssHII/AflII restriction fragment of a vector which comprises SEQ ID NO:2 are provided.

The present invention also provides probes and primers useful for molecular biology techniques. A compound which encodes all or part of SEQ ID NO:1 or the reverse complement of a compound which encodes SEQ ID NO:1, and which is at least 18 consecutive base pairs in length is provided as a probe and/or a primer. Preferably, the 18 base pair or more compound is DNA. Most preferred for this use are the DNA compounds which are SEQ ID NO:3, SEQ ID NO:4 and SEQ ID NO:5, or their reverse complements.

Further, this invention provides cells in which the nucleic acid compounds of the invention may be harbored. For example, oocytes wherein nucleic acid compounds of the invention express functional HSmGluR1 receptor are provided. An oocyte wherein DNA expresses functional HSmGluR1 receptor is preferred. Most preferred is an oocyte wherein sense mRNA expresses functional HSmGluR1 receptor.

Other host cells include those which are transfected with a nucleic acid compound which encodes SEQ ID NO:1. The preferred transfected host cells which encode SEQ ID NO:1 are mammalian cells and *E. Coli*. Preferred mammalian cells include AV12 cells. Preferred host cells are those which have been transfected with a recombinant DNA vector. Preferably, the DNA vector comprises SEQ ID NO:2. The most preferred transfected host cells are AV12/pRS121 and *E. coli*/pRS117.

Additionally, the invention provides a method for identifying nucleic acids homologous to a probe of the present invention, which comprises contacting the test nucleic acid with the probe under hybridizing conditions, and identifying nucleic acids which are homologous to the probe. The preferred probes for use in this method are SEQ ID NO:3, SEQ ID NO:4 or SEQ ID NO:5.

Assays utilizing the compounds provided by the present invention are also provided. The assays provided determine whether a substance interacts with or affects the compound SEQ ID NO:1, said assays comprising contacting a functional compound of SEQ ID NO:1 with said substance, monitoring interaction by physically detectable means, and identifying those substances which effect a chosen response.

Preferably, the physically detectable means are competition with labeled glutamate, hydrolysis of phosphatidylinositol (PI), electrophysiological response in an oocyte expression system, stimulation or inhibition of adenylate cyclase or release of arachidonic acid. A most preferred glutamate competition assay utilizes radioisotopelabeled glutamate. A most preferred oocyte expression system utilizes sense mRNA.

The invention also provides a method for constructing a recombinant host cell capable of expressing a nucleic acid compound which encodes a compound which comprises SEQ ID NO:1, said method comprising transfecting a host cell with a recombinant DNA vector that comprises said nucleic acid compound. The preferred method utilizes mammalian cells as the host cells. The most preferred method utilizes AV12 cells as the mammalian host cells. A preferred method includes a DNA vector which comprises SEQ ID NO:2. A most preferred method utilizes the DNA vector pRS121.

Additionally, a method for expressing a nucleic acid sequence which encodes SEQ ID NO:1 in a recombinant host cell is provided. The method comprises culturing a transfected host cell provided by the present invention under conditions suitable for gene expression. The preferred method utilizes mammalian cells as the host cells. The most preferred method utilizes AV12 cells as the mammalian host cells. The more preferred method utilizes a recombinant DNA vector comprising SEQ ID NO:2. The most preferred method utilizes the recombinant DNA vector pRS121.

The following section provides a detailed description of the present invention. For purposes of clarity and as an aid in understanding the invention, as disclosed and claimed herein, the following items are defined below.

"mRNA"—RNA which has been transcribed either in vivo or in vitro, including, for example, RNA transcripts prepared in vitro via transcription of coding sequences of DNA by RNA polymerase.

"Primer"—A nucleic acid fragment or its reverse complement which functions as template for enzymatic or synthetic elongation.

"Probe"—A nucleic acid compound or a fragment thereof, or its reverse complement either of which is used to hybridize to other nucleic acids.

"Part of SEQ ID NO:1"—A sequence containing at least 6 consecutive amino acid residues or more and that corresponds to a sequence contained in SEQ ID NO:1.

"Physically detectable"—Any information which has been presented in humanly recognizable form, with or without the aid of intervening interpretation. For example, electrophysiological, chemical or biochemical data is considered within the realm of physically detectable information.

"Functional compound of SEQ ID NO:1"—A compound comprising SEQ ID NO:1 which is capable of interacting with glutamate.

"HSmGluR1 receptor"—the amino acid sequence SEQ ID NO:1.

"SEQ ID NO:1 and functional equivalents thereof"—The compound of SEQ ID NO:1 and conserved alterations of the amino acid sequence of SEQ ID NO:1, wherein the conserved alterations result in a compound which exhibits substantially the same physical and structural qualities of SEQ ID:1.

"SEQ ID NO:3"—The DNA sequence ATG GTC GGG CTC CTT TTG TTT TTT TTC CCA GCG ATC TTT TTG GAG GTG TCC CTT CTC CCC. This sequence includes bases 1 through 60 of SEQ ID NO:2.

"SEQ ID NO:4"—CCA GGA CACCTT CTG GAA AAT CCC AAC TTT AAA CGA ATC TGC ACA GGC AAT GAA AGC TTA. This sequence includes bases 1141 through 1200 of SEQ ID NO:2.

"SEQ ID NO:5"—AAC GTA TCC TAC GCC TCT GTC ATT CTC CGG GAC TAC AAG CAA AGC TCT TCC ACC CTG TAA. This sequence includes bases 3761 through 3817 of SEQ ID NO:2, with the addition of a TAA stop codon at the 3' end.

"Transfection"—any transfer of nucleic acid into a host cell, with or without integration of said nucleic acid into genome of said host cell.

DETAILED DESCRIPTION OF THE INVENTION

The present invention provides compounds which comprise the amino acid sequence SEQ ID NO:1, and functional equivalents thereof. The preferred amino acid compound is SEQ ID NO:1, which is the following sequence of amino acids:

```
Met Val Gly Leu Leu Leu Phe Phe Phe Pro Ala Ile Phe Leu Glu Val
 1               5                   10                  15

Ser Leu Leu Pro Arg Ser Pro Gly Arg Lys Val Leu Leu Ala Gly Ala
            20                  25                  30

Ser Ser Gln Arg Ser Val Ala Arg Met Asp Gly Asp Val Ile Ile Gly
        35                  40                  45

Ala Leu Phe Ser Val His His Gln Pro Pro Ala Glu Lys Val Pro Glu
    50                  55                  60

Arg Lys Cys Gly Glu Ile Arg Glu Gln Tyr Gly Ile Gln Arg Val Glu
65                  70                  75                  80

Ala Met Phe His Thr Leu Asp Lys Ile Asn Ala Asp Pro Val Leu Leu
                85                  90                  95

Pro Asn Ile Thr Leu Gly Ser Glu Ile Arg Asp Ser Cys Trp His Ser
            100                 105                 110

Ser Val Ala Leu Glu Gln Ser Ile Glu Phe Ile Arg Asp Ser Leu Ile
```

-continued

```
            115                 120                 125
Ser Ile Arg Asp Glu Lys Asp Gly Ile Asn Arg Cys Leu Pro Asp Cly
    130                 135                 140
Gln Ser Leu Pro Pro Gly Arg Thr Lys Lys Pro Ile Ala Gly Val Ile
145                 150                 155                 160
Gly Pro Gly Ser Ser Ser Val Ala Ile Gln Val Gln Asn Leu Leu Gln
                165                 170                 175
Leu Phe Asp Ile Pro Gln Ile Ala Tyr Ser Ala Thr Ser Ile Asp Leu
                180                 185                 190
Ser Asp Lys Thr Leu Tyr Lys Tyr Phe Leu Arg Val Val Pro Ser Asp
            195                 200                 205
Thr Leu Gln Ala Arg Ala Met Leu Asp Ile Val Lys Arg Tyr Asn Trp
    210                 215                 220
Thr Tyr Val Ser Ala Val His Thr Glu Gly Asn Tyr Gly Glu Ser Gly
225                 230                 235                 240
Met Asp Ala Phe Lys Glu Leu Ala Ala Gln Glu Gly Leu Cys Ile Ala
                245                 250                 255
His Ser Asp Lys Ile Tyr Ser Asn Ala Gly Glu Lys Ser Phe Asp Arg
                260                 265                 270
Leu Leu Arg Lys Leu Arg Glu Arg Leu Pro Lys Ala Arg Val Val Val
            275                 280                 285
Cys Phe Cys Glu Gly Met Thr Val Arg Gly Leu Leu Ser Ala Met Arg
    290                 295                 300
Arg Leu Gly Val Val Gly Glu Phe Ser Leu Ile Gly Ser Asp Gly Trp
305                 310                 315                 320
Ala Asp Arg Asp Glu Val Ile Glu Gly Tyr Glu Val Glu Ala Asn Gly
                325                 330                 325
Gly Ile Thr Ile Lys Leu Gln Ser Pro Glu Val Arg Ser Phe Asp Asp
                340                 345                 350
Tyr Phe Leu Lys Leu Arg Leu Asp Thr Asn Thr Arg Asn Pro Trp Phe
            355                 360                 365
Pro Glu Phe Trp Gin His Arg Phe Gln Cys Arg Leu Pro Gly His Leu
    370                 375                 380
Leu Glu Asn Pro Asn Phe Lys Arg Ile Cys Thr Gly Asn Glu Ser Leu
385                 390                 395                 400
Glu Glu Asn Tyr Val Gln Asp Ser Lys Met Gly Phe Val Ile Asn Ala
                405                 410                 415
Ile Tyr Ala Met Ala His Gly Leu Gln Asn Met His His Ala Leu Cys
                420                 425                 430
Pro Gly His Val Gly Leu Cys Asp Ala Met Lys Pro Ile Asp Gly Ser
            435                 440                 445
Lys Leu Leu Asp Phe Leu Ile Lys Ser Ser Phe Ile Gly Val Ser Gly
    450                 455                 460
Glu Glu Val Trp Phe Asp Glu Lys Gly Asp Ala Pro Gly Arg Tyr Asp
465                 470                 475                 480
Ile Met Asn Leu Gln Tyr Thr Glu Ala Asn Arg Tyr Asp Tyr Val His
                485                 490                 495
Val Gly Thr Trp His Glu Gly Val Leu Asn Ile Asp Asp Tyr Lys Ile
                500                 505                 510
Gln Met Asn Lys Ser Gly Val Val Arg Ser Val Cys Ser Glu Pro Cys
            515                 520                 525
Leu Lys Gly Gln Ile Lys Val Ile Arg Lys Gly Glu Val Ser Cys Cys
    530                 535                 540
```

-continued

Trp Ile Cys Thr Ala Cys Lys Glu Asn Glu Tyr Val Gln Asp Glu Phe
545                 550                 555                 560

Thr Cys Lys Ala Cys Asp Leu Gly Trp Trp Pro Asn Ala Asp Leu Thr
            565                 570                 575

Gly Cys Glu Pro Ile Pro Val Arg Tyr Leu Glu Trp Ser Asn Ile Glu
        580                 585                 590

Pro Ile Ile Ala Ile Ala Phe Ser Cys Leu Gly Ile Leu Val Thr Leu
    595                 600                 605

Phe Val Thr Leu Ile Phe Val Leu Tyr Arg Asp Thr Pro Val Val Lys
610                 615                 620

Ser Ser Ser Arg Glu Leu Cys Tyr Ile Ile Leu Ala Gly Ile Phe Leu
625                 630                 635                 640

Gly Tyr Val Cys Pro Phe Thr Leu Ile Ala Lys Pro Thr Thr Thr Ser
                645                 650                 655

Cys Tyr Leu Gln Arg Leu Leu Val Gly Leu Ser Ser Ala Met Cys Tyr
            660                 665                 670

Ser Ala Leu Val Thr Lys Thr Asn Arg Ile Ala Arg Ile Leu Ala Gly
        675                 680                 685

Ser Lys Lys Lys Ile Cys Thr Arg Lys Pro Arg Phe Met Ser Ala Trp
690                 695                 700

Ala Gln Val Ile Ile Ala Ser Ile Leu Ile Ser Val Gln Leu Thr Leu
705                 710                 715                 720

Val Val Thr Leu Ile Ile Met Glu Pro Pro Met Pro Ile Leu Ser Tyr
                725                 730                 735

Pro Ser Ile Lys Glu Val Tyr Leu Ile Cys Asn Thr Ser Asn Leu Gly
            740                 745                 750

Val Val Ala Pro Leu Gly Tyr Asn Gly Leu Leu Ile Met Ser Cys Thr
        755                 760                 765

Tyr Tyr Ala Phe Lys Thr Arg Asn Val Pro Ala Asn Phe Asn Glu Ala
770                 775                 780

Lys Tyr Ile Ala Phe Thr Met Tyr Thr Thr Cys Ile Ile Trp Leu Ala
785                 790                 795                 800

Phe Val Pro Ile Tyr Phe Gly Ser Asn Tyr Lys Ile Ile Thr Thr Cys
                805                 810                 815

Phe Ala Val Ser Leu Ser Val Thr Val Ala Leu Gly Cys Met Phe Thr
            820                 825                 830

Pro Lys Met Tyr Ile Ile Ala Lys Pro Glu Arg Asn Val Arg Ser
        835                 840                 845

Ala Phe Thr Thr Ser Asp Val Val Arg Met His Val Gly Asp Gly Lys
850                 855                 860

Leu Pro Cys Arg Ser Asn Thr Phe Leu Asn Ile Phe Arg Arg Lys Lys
865                 870                 875                 880

Ala Gly Ala Gly Asn Ala Asn Ser Asn Gly Lys Ser Val Ser Trp Ser
                885                 890                 895

Glu Pro Gly Gly Gly Gln Val Pro Lys Gly Gln His Met Trp His Arg
            900                 905                 910

Leu Ser Val His Val Lys Thr Asn Glu Thr Ala Cys Asn Gln Thr Ala
        915                 920                 925

Val Ile Lys Pro Leu Thr Lys Ser Tyr Gln Gly Ser Gly Lys Ser Leu
930                 935                 940

Thr Phe Ser Asp Thr Ser Thr Lys Thr Leu Tyr Asn Val Glu Glu
945                 950                 955                 960

Glu Asp Ala Gln Pro Ile Arg Phe Ser Pro Pro Gly Ser Pro Ser Met
                965                 970                 975

-continued

```
Val Val His Arg Arg Val Pro Ser Ala Ala Thr Thr Pro Pro Leu Pro
            980             985             990

Pro His Leu Thr Ala Glu Glu Thr Pro Leu Phe Leu Ala Glu Pro Ala
        995            1000            1005

Leu Pro Lys Gly Leu Pro Pro Leu Gln Gln Gln Gln Gln Pro Pro
    1010            1015            1020

Pro Gln Gln Lys Ser Leu Met Asp Gln Leu Gln Gly Val Val Ser Asn
1025            1030            1035            1040

Phe Ser Thr Ala Ile Pro Asp Phe His Ala Val Leu Ala Gly Pro Gly
            1045            1050            1055

Gly Pro Gly Asn Gly Leu Arg Ser Leu Tyr Pro Pro Pro Pro Pro
            1060            1065            1070

Gln His Leu Gln Met Leu Pro Leu Gln Leu Ser Thr Phe Gly Glu Glu
        1075            1080            1085

Leu Val Ser Pro Pro Ala Asp Asp Asp Asp Ser Glu Arg Phe Lys
        1090            1095            1100

Leu Leu Gln Glu Tyr Val Tyr Glu His Glu Arg Glu Gly Asn Thr Glu
1105            1110            1115            1120

Glu Asp Glu Leu Glu Glu Glu Glu Asp Leu Gln Ala Ala Ser Lys
            1125            1130            1135

Leu Thr Pro Asp Asp Ser Pro Ala Leu Thr Pro Pro Ser Pro Phe Arg
            1140            1145            1150

Asp Ser Val Ala Ser Gly Ser Ser Val Pro Ser Ser Pro Val Ser Glu
            1155            1160            1165

Ser Val Leu Cys Thr Pro Pro Asn Val Ser Tyr Ala Ser Val Ile Leu
    1170            1175            1180

Arg Asp Tyr Lys Gln Ser Ser Ser Thr Leu
1185            1190
```

Those in the art will recognize that some alterations of SEQ ID NO:1 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also included in the present invention.

Artisans will also recognize that SEQ ID NO:1 and functional equivalents thereof may be synthesized by a number of different methods. All of the amino acid compounds of the invention can be made by chemical methods well known in the art, including solid phase peptide synthesis or recombinant methods. Both methods are described in U.S. Pat. No. 4,617,149. Recombinant methods are preferred if a high yield is desired. A general method for the construction of any desired DNA sequence is provided in Brown et al., 68 *Methods in Enzymology* 109 (1979).

Other routes of producing the amino acid compounds are well known. Expression in eucaryotic cells can be achieved via SEQ ID NO:2. For example, the amino acid compounds can be produced in eucaryotic cells using SV40-derived expression vectors comprising DNA which encodes for SEQ ID NO:1. Some viruses are also appropriate vectors for this purpose. For example, the adenovirus, the adeno associated virus, the vaccinia virus, the herpes virus, the baculovirus, and the Rous sarcoma virus are useful viral vectors. Such a method is described in U.S Pat. No. 4,775,624. Several alternate methods of expression are described in J. Sambrook, E. F. Fritsch & T. Maniatis, *Molecular Cloning: A Laboratory Manual* 16.3–17.44 (1989).

Other embodiments of the present invention are nucleic acid compounds which comprise nucleic acid sequences which encode SEQ ID NO:1. As those in the art will recognize, the amino acid compounds of the invention can be encoded by a multitude of different nucleic acid sequences because most of the amino acids are encoded by more than one nucleic acid triplet. Because these alternate nucleic acid sequences would encode the same amino acid sequences, the present invention further comprises these alternate nucleic acid sequences. Preferably, the nucleic acid compound is DNA or sense mRNA. A most preferred embodiment of a DNA compound encoding an HSmGluR1 receptor has this sequence:

```
ATGGTCGGGC TCCTTTTGTT TTTTTTCCCA GCGATCTTTT TGGAGGTGTC CCTTCTCCCC    60
AGAAGCCCCG GCAGGAAAGT GTTGCTGGCA GGAGCGTCGT CTCAGCGCTC GGTGGCCAGA   120
ATGGACGGAG ATGTCATCAT TGGAGCCCTC TTCTCAGTCC ATCACCAGCC TCCGGCCGAG   180
```

-continued

```
AAAGTGCCCG AGAGGAAGTG TGGGGAGATC AGGGAGCAGT ATGGCATCCA GAGGGTGGAG    240
GCCATGTTCC ACACGTTGGA TAAGATCAAC GCGGACCCGG TCCTCCTGCC CAACATCACC    300
CTGGGCAGTG AGATCCGGGA CTCCTGCTGG CACTCTTCCG TGGCTCTGGA ACAGAGCATT    360
GAGTTCATTA GGGACTCTCT GATTTCCATT CGAGATGAGA AGGATGGGAT CAACCGGTGT    420
CTGCCTGACG GCCAGTCCCT CCCCCCAGGC AGGACTAAGA AGCCCATTGC GGGAGTGATC    480
GGTCCCGGCT CCAGCTCTGT AGCCATTCAA GTGCAGAACC TGCTCCAGCT CTTCGACATC    540
CCCCAGATCG CTTATTCAGC CACAAGCATC GACCTGAGTG ACAAAACTTT GTACAAATAC    600
TTCCTGAGGG TTGTCCCTTC TGACACTTTG CAGGCAAGGG CCATGCTTGA CATAGTCAAA    660
CGTTACAATT GGACCTATGT CTCTGCAGTC CACACGGAAG GGAATTATGG GGAGAGCGGA    720
ATGGACGCTT TCAAAGAGCT GGCTGCCCAG GAAGGCCTCT GTATCGCCCA TTCTGACAAA    780
ATCTACAGCA ACGCTGGGGA GAAGAGCTTT GACCGACTCT GCGCAAACT CCGAGAGAGG    840
CTTCCCAAGG CTAGAGTGGT GGTCTGCTTC TGTGAAGGCA TGACAGTGCG AGGACTCCTG    900
AGCGCCATGC GGCGCCTTGG CGTCGTGGGC GAGTTCTCAC TCATTGGAAG TGATGGATGG    960
GCAGACAGAG ATGAAGTCAT TGAAGGTTAT GAGGTGGAAG CCAACGGGGG AATCACGATA   1020
AAGCTGCAGT CTCCAGAGGT CAGGTCATTT GATGATTATT TCCTGAAACT GAGGCTGGAC   1080
ACTAACACGA GGAATCCCTG GTTCCCTGAG TTCTGGCAAC ATCGGTTCCA GTGCCGCCTT   1140
CCAGGACACC TTCTGGAAAA TCCCAACTTT AAACGAATCT GCACAGGCAA TGAAAGCTTA   1200
GAAGAAAACT ATGTCCAGGA CAGTAAGATG GGGTTTGTCA TCAATGCCAT CTATGCCATG   1260
GCACATGGGC TGCAGAACAT GCACCATGCC CTCTGCCCTG GCCACGTGGG CCTCTGCGAT   1320
GCCATGAAGC CCATCGACGG CAGCAAGCTG CTGGACTTCC TCATCAAGTC CTCATTCATT   1380
GGAGTATCTG GAGAGGAGGT GTGGTTTGAT GAGAAAGGAG ACGCTCCTGG AAGGTATGAT   1440
ATCATGAATC TGCAGTACAC TGAAGCTAAT CGCTATGACT ATGTGCACGT GGAACCTGG    1500
CATGAAGGAG TGCTGAACAT TGATGATTAC AAAATCCAGA TGAACAAGAG TGGAGTGGTG   1560
CGGTCTGTGT GCAGTGAGCC TTGCTTAAAG GGCCAGATTA AGGTTATACG GAAAGGAGAA   1620
GTGAGCTGCT GCTGGATTTG CACGGCCTGC AAAGAGAATG AATATGTGCA AGATGAGTTC   1680
ACCTGCAAAG CTTGTGACTT GGGATGGTGG CCCAATGCAG ATCTAACAGG CTGTGAGCCC   1740
ATTCCTGTGC GCTATCTTGA GTGGAGCAAC ATCGAACCCA TTATAGCCAT CGCCTTTTCA   1800
TGCCTGGGAA TCCTTGTTAC CTTGTTTGTC ACCCTAATCT TTGTACTGTA CCGGGACACA   1860
CCAGTGGTCA AATCCTCCAG TCGGGAGCTC TGCTACATCA TCCTAGCTGG CATCTTCCTT   1920
GGTTATGTGT GCCCATTCAC TCTCATTGCC AAACCTACTA CCACCTCCTG CTACCTCCAG   1980
CGCCTCTTGG TTGGCCTCTC CTCTGCGATG TGCTACTCTG CTTTAGTGAC TAAAACCAAT   2040
CGTATTGCAC GCATCCTGGC TGGCAGCAAG AAGAAGATCT GCACCCGGAA GCCCAGGTTC   2100
ATGAGTGCCT GGGCTCAGGT GATCATTGCC TCAATTCTGA TTAGTGTGCA ACTAACCCTG   2160
GTGGTAACCC TGATCATCAT GGAACCCCCT ATGCCCATTC TGTCCTACCC AAGTATCAAG   2220
GAAGTCTACC TTATCTGCAA TACCAGCAAC CTGGGTGTGG TGGCCCCTTT GGGCTACAAT   2280
GGACTCCTCA TCATGAGCTG TACCTACTAT GCCTTCAAGA CCCGCAACGT GCCCGCCAAC   2340
TTCAACGAGG CCAAATATAT CGCGTTCACC ATGTACACCA CCTGTATCAT CTGGCTAGCT   2400
TTTGTGCCCA TTTACTTTGG GAGCAACTAC AAGATCATCA CAACTTGCTT TGCAGTGAGT   2460
CTCAGTGTAA CAGTGGCTCT GGGGTGCATG TTCACTCCCA AGATGTACAT CATTATTGCC   2520
AAGCCTGAGA GGAATGTCCG CAGTGCCTTC ACCACCTCTG ATGTTGTCCG CATGCATGTT   2580
```

```
                                    -continued
GGCGATGGCA  AGCTGCCCTG  CCGCTCCAAC  ACTTTCCTCA  ACATCTTCCG  AAGAAAGAAG    2640

GCAGGGGCAG  GGAATGCCAA  TTCTAATGGC  AAGTCTGTGT  CATGGTCTGA  ACCAGGTGGA    2700

GGACAGGTGC  CCAAGGGACA  GCATATGTGG  CACCGCCTCT  CTGTGCACGT  GAAGACCAAT    2760

GAGACGGCCT  GCAACCAAAC  AGCCGTCATC  AAACCCCTCA  CTAAAAGTTA  CCAAGGCTCT    2820

GGCAAGAGCC  TGACCTTTTC  AGATACCAGC  ACCAAGACCC  TTTACAACGT  AGAGGAGGAG    2880

GAGGATGCCC  AGCCGATTCG  CTTTAGCCCG  CCTGGTAGCC  CTTCCATGGT  GGTGCACAGG    2940

CGCGTGCCAA  GCGCGGCGAC  CACTCCGCCT  CTGCCGCCCC  ACCTGACCGC  AGAGGAGACC    3000

CCCCTCTTCC  TGGCCGAACC  AGCCCTCCCC  AAGGGCTTGC  CCCCTCCTCT  CCAGCAGCAG    3060

CAGCAACCCC  CTCCACAGCA  GAAATCGCTG  ATGGACCAGC  TCCAGGGAGT  GGTCAGCAAC    3120

TTCAGTACCG  CGATCCCGGA  TTTTCACGCG  GTGCTGGCAG  GCCCCGGGGG  TCCCGGGAAC    3180

GGGCTGCGGT  CCCTGTACCC  GCCCCCGCCA  CCTCCGCAGC  ACCTGCAGAT  GCTGCCGCTG    3240

CAGCTGAGCA  CCTTTGGGGA  GGAGCTGGTC  TCCCCGCCCG  CGGACGACGA  CGACGACAGC    3300

GAGAGGTTTA  AGCTCCTCCA  GGAGTACGTG  TATGAGCACG  AGCGGGAAGG  GAACACCGAA    3360

GAAGACGAAC  TGGAAGAGGA  GGAGGAGGAC  CTGCAGGCGG  CCAGCAAACT  GACCCCGGAT    3420

GATTCGCCTG  CGCTGACGCC  TCCGTCGCCT  TTCCGCGACT  CGGTGGCCTC  GGGCAGCTCG    3480

GTGCCCAGCT  CCCCAGTGTC  CGAGTCGGTG  CTCTGCACCC  CTCCCAACGT  ATCCTACGCC    3540

TCTGTCATTC  TGCGGGACTA  CAAGCAAAGC  TCTTCCACCC  TG
```

This is the sequence identified as SEQ ID NO:2.

E. coli/pRS117, which contains a cloning vector comprising SEQ ID NO:2, was deposited and made part of the stock culture collection of the Northern Regional Research Laboratories (NRRL), Agricultural Research Service, U.S. Department of Agriculture, Peoria, Ill., 61604 on Apr. 22, 1992, under the accession number NRRL B-18969. SEQ ID NO:2 can be isolated from the plasmid, for example, as a 4.1 kb EcoRI restriction fragment. Other fragments may also be useful in obtaining SEQ ID NO:2.

Additionally, the DNA sequences can be synthesized using automated DNA synthesizers, such as the ABS (Applied Biosystems, 850 Lincoln Centre Drive, Foster City, Calif. 94404) 380B DNA synthesizer. The DNA sequences can also be generated by the polymerase chain reaction (PCR) as described in U.S. Pat. No. 4,889,818.

As art workers will recognize, many vectors are available for expression and cloning. Those expression and cloning vectors which comprise nucleic acids which encode SEQ ID NO:1 are included in the present invention. Preferred nucleic acid vectors are those which are DNA. A most preferred recombinant DNA vector comprises the DNA sequence SEQ ID NO:2. Plasmid pRS117 is a preferred DNA vector of the present invention.

Other preferred DNA vectors include those which comprise a promoter positioned to drive expression of SEQ ID NO:2. Preferred expression vectors include those which function in mammalian cells. Preferred mammalian expression vectors include those which function in AV12 cells. Most preferred for expression in AV12 cells is the expression vector pRS121.

Restriction fragments of these vectors are also provided. The preferred fragments are the 4.1 kb EcoRI restriction fragment and the 3.8 kb BssHII/AflII restriction fragment of plasmid pRS117.

Plasmid pRS117 may be isolated from the deposited E. coli/pRS117, using an ordinary cesium chloride DNA isolation procedure. Plasmid pRS117 is readily modified to construct expression vectors that produce HSmGluR1 receptors in a variety of organisms, including, for example, E. coli, Sf9 (as host for baculovirus), Spodoptera and Saccharomycetes. The current literature contains techniques for constructing AV12 expression vectors and for transfecting AV12 host cells. For example, U.S. Pat. No. 4,992,373 explains these techniques.

The construction protocols utilized for AV12 vectors can be followed to construct analogous vectors for other organisms, merely by substituting, if necessary, the appropriate regulatory elements using well known techniques. Promoters which may be used, for example, are the thymidine kinase promoter, the metallothionin promoter or various viral and immunoglobulin promoters.

The present invention also provides probes and primers useful for molecular biology techniques. A compound which encodes all or part of SEQ ID NO:1, or the reverse complement of a compound which encodes SEQ ID NO:1, and which is at least 18 consecutive base pairs in length is provided as a probe and/or a primer. Preferred probes and primers are DNA. Most preferred probes and primers are: SEQ ID NO:3, SEQ ID NO:4 and SEQ ID NO:5. The techniques associated with using probes and primers are well known in the art.

Any sequence of at least 18 base pairs in length of the nucleic acids of the present invention may be used to screen any other nucleic acid. For example, 18 consecutive bases or more of nucleic acids of the present invention may be used to hybridize to the terminal ends of the coding sequence. Then, through polymerase chain reaction amplification, the full length sequence may be generated. The full length sequence can be subsequently subcloned into any vector of choice.

Alternatively, SEQ ID NO:3, SEQ ID NO:4, or SEQ ID NO:5 may be radioactively labeled in order to screen cDNA libraries by conventional means. Furthermore, any piece of HSmGluR1 DNA which has been bound to a filter may be flooded with total mRNA transcripts, in order to then reverse-transcribe the mRNA transcripts which bind.

Primers and probes may be obtained by means well known in the art. For example, once pRS117 is isolated, restriction enzymes and subsequent gel separation may be used to isolate the fragment of choice.

Host cells which harbor the nucleic acids of the present invention are also provided. For example, oocytes which have been injected with RNA or DNA compounds of the present invention are provided. Most preferred oocytes of the present invention are those which harbor sense mRNA. Other preferred host cells include AV12 and *E. Coli* cells which have been transfected with a vector which comprises SEQ ID NO:2. Most preferred AV12 and *E. coli* host cells are AV12/pRS121 and *E. coli*/pRS117.

The oocyte expression system can be constructed according to the procedure described in Lübbert, et al. 84 Proc. Nat. Acad. Sci. 4332 (1987) or Berger, Methods in Enzymology, Vol. 152 (1987). Other host cell transfection methods are well known in the art as well.

The present invention also provides a method for constructing a recombinant host cell capable of expressing SEQ ID NO:1, said method comprising transfecting a host cell with a recombinant DNA vector that comprises an DNA sequence which encodes SEQ ID NO:1.

The preferred host cell is AV12, which may be obtained from the American Type Culture Collection (ATCC) 12301 Parklawn Drive, Rockville, Md. 20852 under the accession number ATCC CRL 9595. The preferred vector for expression is one which comprises SEQ ID NO:2. Especially preferred for this purpose is pRS121.

Other preferred host cells for this method are mammalian cells. Especially preferred mammalian cells are AV12 cells. A preferred AV12 expression vector is pRS121. Transfected host cells may be cultured under well known conditions such that SEQ ID NO:1 is expressed, thus producing HSmGluR1 activity in the recombinant host cell.

Therefore, also provided by the present invention is a method for expressing a gene which encodes SEQ ID NO:1 in a recombinant host cell, said method comprising culturing said transfected host cell under conditions suitable for gene expression. A preferred method utilizes mammalian cells. A preferred method utilizes AV12 cells as the mammalian cells. A most preferred method utilizes AV12 cells as host cells for pRS121. Expression in host cells may be accomplished according to the procedures outlined in Goeddel, *Methods in Enzymology*, Vol. 185 (1990).

Additionally, the invention provides a method for identifying nucleic acids homologous to a probe of the present invention, which comprises contacting a test nucleic acid with the probe under hybridizing conditions and identifying those test nucleic acids which are homologous to the probe. The preferred probes for use in this method are SEQ ID NO:3, SEQ ID:4 or SEQ ID NO:5. Hybridization techniques are well known in the art. Sambrook, et al., *Molecular Cloning: A Laboratory Manual* 11 (1989) describe such procedures.

Assays utilizing the compounds provided by the present invention are also provided. These assays determine whether a substance interacts with or affects the compound of SEQ ID NO:1, said assay comprising contacting a functional compound of SEQ ID NO:1 with said substance, monitoring interaction by physically detectable means, and identifying those substances which effect a chosen response.

Preferably, the physically detectable means are competition with labeled glutamate, hydrolysis of phosphatidylinositol, electrophysiological response in an oocyte expression system, stimulation or inhibition of adenylate cyclase or release of arachidonic acid. A most preferred glutamate competition assay utilizes radioisotope-labeled glutamate. A most preferred oocyte expression system utilizes sense mRNA.

The oocyte expression system can be constructed according to the procedure described in Lübbert, et al. 84 *Proc. Nat. Acad. Sci.* 4332 (1987) or Berger, *Methods in Enzymology*, Vol. 152 (1987) The radiolabeled HSmGluR1 competition assay may be accomplished according to Foster and Fagg, 7 *Brain Res. Rev.* 103 (1984). The assay which measures glutaminergic activity via phosphatidylinositol hydrolysis may be accomplished according to Berridge M., 212 *Biochem. J.* 849 (1983) or Schoepp et al., 11 *TiPS* 508 (1990). Stimulation and inhibition of adenylate cyclase may be measured according to Nakajima et al., 267 *J. Biol. Chem.* 2437 (1992). Measurement of arachidonic acid release may be accomplished according to Felder et al., 264 *J. Biol. Chem.* 20356 (1989).

Skilled artisans will recognize that desirable $K_i$ values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides competition assays, which indicate whether a substance has either a high affinity or low affinity to HSmGluR1 receptor, because skilled artisans will recognize that any information regarding binding or selectivity of a particular compound is beneficial in the pharmaceutical development of drugs.

The following are examples of the present invention:

EXAMPLE 1

Growth of *E. coli*/pRS117

A lyophilized culture of *E. coli* containing plasmid pRS117 can be obtained from the NRRL, Peoria, Ill., 61604, under the accession number NRRL B-18969, and inoculated into a suitable broth for the growth of *E. coli* using standard microbiological procedures.

The contents of a lyophil vial containing *E. coli*/pRS117 were transferred into 100 ml of sterile YT (tryptone-yeast extract) broth containing 100 µg/ml ampicillin in a one liter fermentation flask and shaken at 37° C. on an orbital shaker at 250–300 rpm. After the optical density (OD, measured at 600 millimicrons) had reached approximately 1–2 OD, the bacterial cells were recovered and used for the isolation of plasmid pRS117 according to the procedures detailed in J. Sambrook et al., *Molecular Cloning*, Chapter 1, (1989).

Once isolated from the bacterial cells, the plasmid DNA served as a source for the DNA encoding the HSmGluR1 receptor protein. One convenient method to remove the receptor-encoding DNA from plasmid pRS117 was to digest the plasmid with the restriction enzyme EcoRI. This enzyme cuts the plasmid at unique sites to produce a DNA fragment of approximately 4.1 kb containing the entire coding sequence of the HSmGluR1 receptor.

EXAMPLE 2

Construction of pRS121 from pRS117

DNA encoding SEQ ID NO:1 was recovered from plasmid pRS117 as described in Example 1. DNA linkers were added to the fragment ends in order to adapt the EcoRI cohesive termini into Bam HI cohesive termini. This was accomplished by ligation of short duplex oligonucleotides having both an EcoRI terminus and a BamHI terminus to the pRS117-derived fragments. The ligation involved incubation with T4 DNA ligase.

Following incubation, the reaction products were digested with BamHI and separated according to molecular weight on an agarose gel. The DNA band on the gel at the position expected for a fragment of approximately 4 kb was excised from the gel and the DNA recovered by the phenol-freeze-fracture method of Huff et al., 10 *Biotechniques* 724 (1991).

The isolated fragment was then ligated to a modified pHD plasmid. The modified pHD vector was substantially the vector described in issued U.S. Pat. No. 4,992,373, except that the vector described in the issued patent was digested with the restriction enzyme BclI and treated with alkaline phosphatase. The ligation products were then transfected into *E. coli* DH5α cells which had been made competent for DNA transfection. These cells were plated at low density on TY agar plates which contained ampicillin.

A clone was selected from the colonies which grew. This clone, pRS121 was characterized by restriction enzyme digestion and DNA hybridization probing.

EXAMPLE 3

Transfection and Growth of AV12/pRS121

AV12 cells were grown in a routine manner. Cells were placed in 100 mm cell-culture plates in Dulbecco's modified Eagle's medium (D-MEM) which contained 10% fetal calf serum at 37° C. and grown in an atmosphere containing 5% $CO_2$. To prepare plasmid DNA for transfection, plasmid pRS121 (20 µg) was added to 500 µl of 0.5M $CaCl_2$ and mixed with 500 µl 0.9% NaCl buffered at pH 6.95 with N,N-bis(2-hydroxyethyl)-2-aminoethanesulfonic acid. After 30 minutes at room temperature, the this mixture resulted in a suspension of precipitated DNA.

The suspension of precipitated DNA was then added to a 100 mm diameter cell-culture plate of AV12 cells. At the time of adding the suspension of DNA, the cell monolayer was approximately 50% confluent. The plate was incubated overnight at 37° C. and, after rinsing with D-MEM, the cells were incubated an additional 24 hours in D-MEM containing 10% dialyzed fetal calf serum. The cells were then detached from the plate with trypsin and dispensed into 10 new plates. After an additional 24 hours incubation, hygromycin, at 200 µg/ml final concentration, was added to the growth medium in order to select for colonies of cells which grew. Those cells which grew contained pRS121 with the associated hygromycin resistance gene. After the clones had reached a suitable size, (1–2 mm in diameter), individual clones were recovered and cultures of these clones were propagated using standard tissue-culture techniques. The cultures were grown in a routine manner in D-MEM medium without glutamic acid, containing 2 mM glutamine and 10% dialyzed fetal calf serum. Subcultures were prepared when cultures became confluent. The subculture preparation included disassociating the cells with trypsin, diluting the cells disassociated into fresh culture medium, and placing the dilutions into fresh culture vessels at 1/10 the original concentration.

EXAMPLE 4

AV12/pRS121 PI Assay

PI hydrolysis in clonal cell lines of AV12/pRS121 cells was measured in response to glutamate agonists as a functional assay for metabotropic glutamate receptor activity according to Schoepp, 11 *TiPS* 508 (1990).

Twenty-four-well tissue-culture vessels were seeded with approximately 250,000 cells per well in D-MEM (in the absence of glutamic acid) which contained 2 nM glutamine and 10% dialyzed fetal calf serum. Four microcuries of $^3$H-myoinositol were then added to each well and the cultures were incubated for 48 hours at 37° C. The wells were then rinsed with serum-free medium which contained 10 mM LiCl and 10 mM myoinositol. Some wells were then exposed to medium with glutamate agonists for one hour at 37° C., and some wells were at the same time exposed to medium without glutamate agonists for one hour at 37° C.

The reactions were terminated by removing the media and adding 0.5 ml acetone-methanol (1:1). The cells were then incubated at 4° C. for 20 minutes. The acetone-methanol solutions were recovered from the wells and were placed into centrifuge tubes. Each well was rinsed with 0.5 ml water and the rinses were combined in the centrifuge tubes with the corresponding solvent extracts. After centrifugation at 15,000 g for 10 minutes, the supernatants were recovered.

In order to separate the PI hydrolysis products,. ACELL PLUS QMA (Waters Division of Millipore Corporation) cartridges were prepared by adding 10 ml of a solution containing a final concentration of 1M ammonium formate and 0.1 M formic acid to each cartridge, followed by two rinses with 10 ml distilled water. The cell extracts were were diluted to 5 ml with distilled water and were then added to individual cartridges. Each cartridge was then washed with 10 ml of 5 mm sodium tetraborate solution.

Labeled phosphoinositides were eluted from the cartridges with 4 ml of a solution which contained: 0.1 M ammonium formate; 0.1 M formic acid and 5 mM sodium tetraborate. The eluates were collected in scintillation vials. Scintillation counting fluid (Ready Solv HP) was added to the vials and the radioactivity was determined in a Beckmann Scintillation Counter.

Exposure of the AV12/pRS121 to the known glutamate receptor agonist quisqualate (10 µM) resulted in a 200 to 300 percent increase in PI hydrolysis over the basal level in cells with exposure to agonist. No increase in PI hydrolysis over basal levels was found in control AV12 cells.

EXAMPLE 5

In vitro Transcription of RNA Sing pRS117 as a DNA Template

RNA transcripts encoding the HSmGluR1 receptor were produced by enzymatic transcription from pRS117 using an RNA polymerase which recognizes the transcription promoter contained in the plasmid adjacent to the amino terminal coding end of the receptor subunit cDNA. Plasmid pRS117 was treated with the restriction enzyme SalI which made a single cut distal to the 3' end of the cDNA insert in the circular DNA and converted the plasmid DNA into a linear form. This DNA was then incubated with T7 RNA polymerase in the presence of GpppG cap nucleotide, rATP, rCTP, rUTP and rGTP. The synthetic RNA transcript obtained was purified by passage over a Sephadex G-50 column. For a detailed description of in vitro RNA synthesis using bacteriophage RNA polymerase such as T7, see P. A. Krieg and D. A. Melton, Vol 155, *Methods in Enzymology*, Ch. 25, 1987.

EXAMPLE 6

Functional Expression of HSmGluR1 Receptor in Xenopus Oocytes

Oocytes suitable for injection were obtained from the adult female *Xenopus laevis* using procedures described in C. J. Marcus-Sekura and M. J. M. Hitchcock, *Methods in Enzymology*, Vol. 152 (1987). After treatment with collagenase type 1a (Sigma) at a concentration of 2 mg/ml, the defolliculated oocytes were injected essentially as described by M. J. M. Hitchcock et al., *Methods in Enzymology*, Vol. 152 Chapter 28, (1987). Subsequently, 5 ng of RNA transcript in a total volume of 50 nl, prepared as described in Example 2, were injected into each oocyte and they were then incubated in Barth's saline solution at 18° C. until needed for electrophysiological measurements.

In order to detect the presence of HSmGluR1 receptor, the ability of the receptor to function was determined by voltage recording of electrical current flowing across the oocyte membrane in response to exposure to glutamate agonists. Individual oocytes were placed in a diffusion chamber (0.5 ml vol.) through which solutions were perfused rapidly. Drugs (agonists and antagonists) were applied to the oocytes by adding them to the perfusing solutions and subsequently washing them out with control solution. The control solution contained 96 mM NaCl, 2 mM KCl, 1.8 mM CaCl2, 1 mM MgCl2, and 5 mM HEPES buffer, pH 7.6. After insertion of electrodes into the oocytes, voltage recordings were made using the bridge circuit of an Axoclamp 1A voltage-clamp unit. Microelectrodes were filled with 3 M CsCl. Electrophysiological recordings of the oocytes clamped at −70 mV were made at room temperature (20–25° C.), 3 days or more after injection of RNA into the oocytes. In response to perfusion of the oocytes with 10 $\mu$M glutamate, an inward current across the oocyte membrane of 400 nano-amperes was observed. The current observed was proportional to the concentration of agonist in the perfusion fluid. From the values obtained, $EC_{50}$ values (the concentration at which 50% of maximal response was observed) were calculated for various agonists. For example, the $EC_{50}$ value for glutamate was 0.000002 M, the $EC_{50}$ value for quisqualate was 0.0000004 M and the $EC_{50}$ value for trans-1-amino-1,3-cyclopentane dicarboxylic acid (trans-ACPD) was 0.000065M. As those skilled in the art appreciate these results are indicative of a metabotropic glutamate receptor. For a detailed discussion of the electrophysiology of *Xenopus oocytes* see N. Dascal, 22 CRC *Critical Reviews in Biochemistry*, 317 (1987).

---

What is claimed is:

1. An isolated and purified compound which comprises the amino acid sequence identified as SEQ ID NO:1.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1194 amino acids
      (B) TYPE: amino acid
      (D) TOPOLOGY: linear (ii) MOLECULE TYPE: protein (xi) SEQUENCE DESCRIPTION: SEQ ID NO:1:

```
Met Val Gly Leu Leu Leu Phe Phe Phe Pro Ala Ile Phe Leu Glu Val
1               5                   10                  15

Ser Leu Leu Pro Arg Ser Pro Gly Arg Lys Val Leu Leu Ala Gly Ala
                20                  25                  30

Ser Ser Gln Arg Ser Val Ala Arg Met Asp Gly Asp Val Ile Ile Gly
                35                  40                  45

Ala Leu Phe Ser Val His His Gln Pro Pro Ala Glu Lys Val Pro Glu
    50                  55                  60

Arg Lys Cys Gly Glu Ile Arg Glu Gln Tyr Gly Ile Gln Arg Val Glu
65                  70                  75                  80

Ala Met Phe His Thr Leu Asp Lys Ile Asn Ala Asp Pro Val Leu Leu
                85                  90                  95

Pro Asn Ile Thr Leu Gly Ser Glu Ile Arg Asp Ser Cys Trp His Ser
                100                 105                 110

Ser Val Ala Leu Glu Gln Ser Ile Glu Phe Ile Arg Asp Ser Leu Ile
                115                 120                 125

Ser Ile Arg Asp Glu Lys Asp Gly Ile Asn Arg Cys Leu Pro Asp Gly
        130                 135                 140

Gln Ser Leu Pro Pro Gly Arg Thr Lys Lys Pro Ile Ala Gly Val Ile
145                 150                 155                 160

Gly Pro Gly Ser Ser Ser Val Ala Ile Gln Val Gln Asn Leu Leu Gln
                165                 170                 175
```

```
Leu Phe Asp Ile Pro Gln Ile Ala Tyr Ser Ala Thr Ser Ile Asp Leu
            180                 185                 190

Ser Asp Lys Thr Leu Tyr Lys Tyr Phe Leu Arg Val Val Pro Ser Asp
            195                 200                 205

Thr Leu Gln Ala Arg Ala Met Leu Asp Ile Val Lys Arg Tyr Asn Trp
            210                 215                 220

Thr Tyr Val Ser Ala Val His Thr Glu Gly Asn Tyr Gly Glu Ser Gly
225                 230                 235                 240

Met Asp Ala Phe Lys Glu Leu Ala Ala Gln Glu Gly Leu Cys Ile Ala
            245                 250                 255

His Ser Asp Lys Ile Tyr Ser Asn Ala Gly Glu Lys Ser Phe Asp Arg
            260                 265                 270

Leu Leu Arg Lys Leu Arg Glu Arg Leu Pro Lys Ala Arg Val Val Val
            275                 280                 285

Cys Phe Cys Glu Gly Met Thr Val Arg Gly Leu Leu Ser Ala Met Arg
            290                 295                 300

Arg Leu Gly Val Val Gly Glu Phe Ser Leu Ile Gly Ser Asp Gly Trp
305                 310                 315                 320

Ala Asp Arg Asp Glu Val Ile Glu Gly Tyr Glu Val Glu Ala Asn Gly
            325                 330                 335

Gly Ile Thr Ile Lys Leu Gln Ser Pro Glu Val Arg Ser Phe Asp Asp
            340                 345                 350

Tyr Phe Leu Lys Leu Arg Leu Asp Thr Asn Thr Arg Asn Pro Trp Phe
            355                 360                 365

Pro Glu Phe Trp Gln His Arg Phe Gln Cys Arg Leu Pro Gly His Leu
            370                 375                 380

Leu Glu Asn Pro Asn Phe Lys Arg Ile Cys Thr Gly Asn Glu Ser Leu
385                 390                 395                 400

Glu Glu Asn Tyr Val Gln Asp Ser Lys Met Gly Phe Val Ile Asn Ala
            405                 410                 415

Ile Tyr Ala Met Ala His Gly Leu Gln Asn Met His His Ala Leu Cys
            420                 425                 430

Pro Gly His Val Gly Leu Cys Asp Ala Met Lys Pro Ile Asp Gly Ser
            435                 440                 445

Lys Leu Leu Asp Phe Leu Ile Lys Ser Ser Phe Ile Gly Val Ser Gly
            450                 455                 460

Glu Glu Val Trp Phe Asp Glu Lys Gly Asp Ala Pro Gly Arg Tyr Asp
465                 470                 475                 480

Ile Met Asn Leu Gln Tyr Thr Glu Ala Asn Arg Tyr Asp Tyr Val His
            485                 490                 495

Val Gly Thr Trp His Glu Gly Val Leu Asn Ile Asp Asp Tyr Lys Ile
            500                 505                 510

Gln Met Asn Lys Ser Gly Val Val Arg Ser Val Cys Ser Glu Pro Cys
            515                 520                 525

Leu Lys Gly Gln Ile Lys Val Ile Arg Lys Gly Glu Val Ser Cys Cys
            530                 535                 540

Trp Ile Cys Thr Ala Cys Lys Glu Asn Glu Tyr Val Gln Asp Glu Phe
545                 550                 555                 560

Thr Cys Lys Ala Cys Asp Leu Gly Trp Trp Pro Asn Ala Asp Leu Thr
            565                 570                 575

Gly Cys Glu Pro Ile Pro Val Arg Tyr Leu Glu Trp Ser Asn Ile Glu
            580                 585                 590
```

```
Pro Ile Ile Ala Ile Ala Phe Ser Cys Leu Gly Ile Leu Val Thr Leu
            595                 600                 605

Phe Val Thr Leu Ile Phe Val Leu Tyr Arg Asp Thr Pro Val Val Lys
            610                 615                 620

Ser Ser Ser Arg Glu Leu Cys Tyr Ile Ile Leu Ala Gly Ile Phe Leu
625                 630                 635                 640

Gly Tyr Val Cys Pro Phe Thr Leu Ile Ala Lys Pro Thr Thr Thr Ser
            645                 650                 655

Cys Tyr Leu Gln Arg Leu Leu Val Gly Leu Ser Ser Ala Met Cys Tyr
            660                 665                 670

Ser Ala Leu Val Thr Lys Thr Asn Arg Ile Ala Arg Ile Leu Ala Gly
            675                 680                 685

Ser Lys Lys Ile Cys Thr Arg Lys Pro Arg Phe Met Ser Ala Trp
690                 695                 700

Ala Gln Val Ile Ile Ala Ser Ile Leu Ile Ser Val Gln Leu Thr Leu
705                 710                 715                 720

Val Val Thr Leu Ile Ile Met Glu Pro Pro Met Pro Ile Leu Ser Tyr
            725                 730                 735

Pro Ser Ile Lys Glu Val Tyr Leu Ile Cys Asn Thr Ser Asn Leu Gly
            740                 745                 750

Val Val Ala Pro Leu Gly Tyr Asn Gly Leu Leu Ile Met Ser Cys Thr
            755                 760                 765

Tyr Tyr Ala Phe Lys Thr Arg Asn Val Pro Ala Asn Phe Asn Glu Ala
770                 775                 780

Lys Tyr Ile Ala Phe Thr Met Tyr Thr Thr Cys Ile Ile Trp Leu Ala
785                 790                 795                 800

Phe Val Pro Ile Tyr Phe Gly Ser Asn Tyr Lys Ile Ile Thr Thr Cys
            805                 810                 815

Phe Ala Val Ser Leu Ser Val Thr Val Ala Leu Gly Cys Met Phe Thr
            820                 825                 830

Pro Lys Met Tyr Ile Ile Ala Lys Pro Glu Arg Asn Val Arg Ser
            835                 840                 845

Ala Phe Thr Thr Ser Asp Val Val Arg Met His Val Gly Asp Gly Lys
850                 855                 860

Leu Pro Cys Arg Ser Asn Thr Phe Leu Asn Ile Phe Arg Arg Lys Lys
865                 870                 875                 880

Ala Gly Ala Gly Asn Ala Asn Ser Asn Gly Lys Ser Val Ser Trp Ser
            885                 890                 895

Glu Pro Gly Gly Gly Gln Val Pro Lys Gly Gln His Met Trp His Arg
            900                 905                 910

Leu Ser Val His Val Lys Thr Asn Glu Thr Ala Cys Asn Gln Thr Ala
            915                 920                 925

Val Ile Lys Pro Leu Thr Lys Ser Tyr Gln Gly Ser Gly Lys Ser Leu
            930                 935                 940

Thr Phe Ser Asp Thr Ser Thr Lys Thr Leu Tyr Asn Val Glu Glu
945                 950                 955                 960

Glu Asp Ala Gln Pro Ile Arg Phe Ser Pro Gly Ser Pro Ser Met
            965                 970                 975

Val Val His Arg Arg Val Pro Ser Ala Ala Thr Thr Pro Pro Leu Pro
            980                 985                 990

Pro His Leu Thr Ala Glu Glu Thr Pro Leu Phe Leu Ala Glu Pro Ala
            995                 1000                1005

Leu Pro Lys Gly Leu Pro Pro Leu Gln Gln Gln Gln Pro Pro
```

```
            1010              1015              1020
Pro Gln Gln Lys Ser Leu Met Asp Gln Leu Gln Gly Val Val Ser Asn
1025              1030              1035              1040

Phe Ser Thr Ala Ile Pro Asp Phe His Ala Val Leu Ala Gly Pro Gly
                1045              1050              1055

Gly Pro Gly Asn Gly Leu Arg Ser Leu Tyr Pro Pro Pro Pro Pro Pro
            1060              1065              1070

Gln His Leu Gln Met Leu Pro Leu Gln Leu Ser Thr Phe Gly Glu Glu
        1075              1080              1085

Leu Val Ser Pro Pro Ala Asp Asp Asp Asp Ser Glu Arg Phe Lys
    1090              1095              1100

Leu Leu Gln Glu Tyr Val Tyr Glu His Glu Arg Glu Gly Asn Thr Glu
1105              1110              1115              1120

Glu Asp Glu Leu Glu Glu Glu Glu Asp Leu Gln Ala Ala Ser Lys
                1125              1130              1135

Leu Thr Pro Asp Asp Ser Pro Ala Leu Thr Pro Pro Ser Pro Phe Arg
                1140              1145              1150

Asp Ser Val Ala Ser Gly Ser Ser Val Pro Ser Pro Val Ser Glu
        1155              1160              1165

Ser Val Leu Cys Thr Pro Pro Asn Val Ser Tyr Ala Ser Val Ile Leu
    1170              1175              1180

Arg Asp Tyr Lys Gln Ser Ser Ser Thr Leu
1185              1190
```

(2) INFORMATION FOR SEQ ID NO:2:

(i) SEQUENCE CHARACTERISTICS:
        (A) LENGTH: 3582 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..3582

(xi) SEQUENCE DESCRIPTION: SEQ ID NO:2:

```
ATGGTCGGGC TCCTTTTGTT TTTTTTCCCA GCGATCTTTT TGGAGGTGTC CCTTCTCCCC      60

AGAAGCCCCG GCAGGAAAGT GTTGCTGGCA GGAGCGTCGT CTCAGCGCTC GGTGGCCAGA     120

ATGGACGGAG ATGTCATCAT TGGAGCCCTC TTCTCAGTCC ATCACCAGCC TCCGGCCGAG     180

AAAGTGCCCG AGAGGAAGTG TGGGGAGATC AGGGAGCAGT ATGGCATCCA GAGGGTGGAG     240

GCCATGTTCC ACACGTTGGA TAAGATCAAC GCGGACCCGG TCCTCCTGCC CAACATCACC     300

CTGGGCAGTG AGATCCGGGA CTCCTGCTGG CACTCTTCCG TGGCTCTGGA ACAGAGCATT     360

GAGTTCATTA GGGACTCTCT GATTTCCATT CGAGATGAGA AGGATGGGAT CAACCGGTGT     420

CTGCCTGACG GCCAGTCCCT CCCCCCAGGC AGGACTAAGA AGCCCATTGC GGGAGTGATC     480

GGTCCCGGCT CCAGCTCTGT AGCCATTCAA GTGCAGAACC TGCTCCAGCT CTTCGACATC     540

CCCCAGATCG CTTATTCAGC CACAAGCATC GACCTGAGTG ACAAAACTTT GTACAAATAC     600

TTCCTGAGGG TTGTCCCTTC TGACACTTTG CAGGCAAGGG CCATGCTTGA CATAGTCAAA     660

CGTTACAATT GGACCTATGT CTCTGCAGTC CACACGGAAG GGAATTATGG GGAGAGCGGA     720

ATGGACGCTT TCAAAGAGCT GGCTGCCCAG GAAGGCCTCT GTATCGCCCA TTCTGACAAA     780

ATCTACAGCA ACGCTGGGGA GAAGAGCTTT GACCGACTCT GCGCAAACT CCGAGAGAGG     840
```

```
CTTCCCAAGG CTAGAGTGGT GGTCTGCTTC TGTGAAGGCA TGACAGTGCG AGGACTCCTG    900
AGCGCCATGC GGCGCCTTGG CGTCGTGGGC GAGTTCTCAC TCATTGGAAG TGATGGATGG    960
GCAGACAGAG ATGAAGTCAT TGAAGGTTAT GAGGTGGAAG CCAACGGGGG AATCACGATA   1020
AAGCTGCAGT CTCCAGAGGT CAGGTCATTT GATGATTATT TCCTGAAACT GAGGCTGGAC   1080
ACTAACACGA GGAATCCCTG GTTCCCTGAG TTCTGGCAAC ATCGGTTCCA GTGCCGCCTT   1140
CCAGGACACC TTCTGGAAAA TCCCAACTTT AAACGAATCT GCACAGGCAA TGAAAGCTTA   1200
GAAGAAAACT ATGTCCAGGA CAGTAAGATG GGGTTTGTCA TCAATGCCAT CTATGCCATG   1260
GCACATGGGC TGCAGAACAT GCACCATGCC CTCTGCCCTG CCACGTGGG CCTCTGCGAT   1320
GCCATGAAGC CCATCGACGG CAGCAAGCTG CTGGACTTCC TCATCAAGTC CTCATTCATT   1380
GGAGTATCTG GAGAGGAGGT GTGGTTTGAT GAGAAAGGAG ACGCTCCTGG AAGGTATGAT   1440
ATCATGAATC TGCAGTACAC TGAAGCTAAT CGCTATGACT ATGTGCACGT GGAACCTGG    1500
CATGAAGGAG TGCTGAACAT TGATGATTAC AAAATCCAGA TGAACAAGAG TGGAGTGGTG   1560
CGGTCTGTGT GCAGTGAGCC TTGCTTAAAG GGCCAGATTA AGGTTATACG GAAAGGAGAA   1620
GTGAGCTGCT GCTGGATTTG CACGGCCTGC AAAGAGAATG AATATGTGCA AGATGAGTTC   1680
ACCTGCAAAG CTTGTGACTT GGGATGGTGG CCCAATGCAG ATCTAACAGG CTGTGAGCCC   1740
ATTCCTGTGC GCTATCTTGA GTGGAGCAAC ATCGAACCCA TTATAGCCAT CGCCTTTTCA   1800
TGCCTGGGAA TCCTTGTTAC CTTGTTTGTC ACCCTAATCT TTGTACTGTA CCGGGACACA   1860
CCAGTGGTCA AATCCTCCAG TCGGGAGCTC TGCTACATCA TCCTAGCTGG CATCTTCCTT   1920
GGTTATGTGT GCCCATTCAC TCTCATTGCC AAACCTACTA CCACCTCCTG CTACCTCCAG   1980
CGCCTCTTGG TTGGCCTCTC CTCTGCGATG TGCTACTCTG CTTTAGTGAC TAAAACCAAT   2040
CGTATTGCAC GCATCCTGGC TGGCAGCAAG AAGAAGATCT GCACCCGGAA GCCCAGGTTC   2100
ATGAGTGCCT GGGCTCAGGT GATCATTGCC TCAATTCTGA TTAGTGTGCA ACTAACCCTG   2160
GTGGTAACCC TGATCATCAT GGAACCCCCT ATGCCCATTC TGTCCTACCC AAGTATCAAG   2220
GAAGTCTACC TTATCTGCAA TACCAGCAAC CTGGGTGTGG TGGCCCCTTT GGGCTACAAT   2280
GGACTCCTCA TCATGAGCTG TACCTACTAT GCCTTCAAGA CCCGCAACGT GCCCGCCAAC   2340
TTCAACGAGG CCAAATATAT CGCGTTCACC ATGTACACCA CCTGTATCAT CTGGCTAGCT   2400
TTTGTGCCCA TTTACTTTGG GAGCAACTAC AAGATCATCA CAACTTGCTT TGCAGTGAGT   2460
CTCAGTGTAA CAGTGGCTCT GGGGTGCATG TTCACTCCCA AGATGTACAT CATTATTGCC   2520
AAGCCTGAGA GGAATGTCCG CAGTGCCTTC ACCACCTCTG ATGTTGTCCG CATGCATGTT   2580
GGCGATGGCA AGCTGCCCTG CCGCTCCAAC ACTTTCCTCA ACATCTTCCG AAGAAAGAAG   2640
GCAGGGGCAG GGAATGCCAA TTCTAATGGC AAGTCTGTGT CATGGTCTGA ACCAGGTGGA   2700
GGACAGGTGC CAAGGGACA GCATATGTGG CACCGCCTCT CTGTGCACGT GAAGACCAAT   2760
GAGACGGCCT GCAACCAAAC AGCCGTCATC AAACCCCTCA CTAAAAGTTA CCAAGGCTCT   2820
GGCAAGAGCC TGACCTTTTC AGATACCAGC ACCAAGACCC TTTACAACGT AGAGGAGGAG   2880
GAGGATGCCC AGCCGATTCG CTTTAGCCCG CCTGGTAGCC CTTCCATGGT GGTGCACAGG   2940
CGCGTGCCAA GCGCGGCGAC CACTCCGCCT CTGCCGCCCC ACCTGACCGC AGAGGAGACC   3000
CCCCTCTTCC TGGCCGAACC AGCCCTCCCC AAGGGCTTGC CCCCTCCTCT CCAGCAGCAG   3060
CAGCAACCCC CTCCACAGCA GAAATCGCTG ATGGACCAGC TCCAGGGAGT GGTCAGCAAC   3120
TTCAGTACCG CGATCCCGGA TTTTCACGCG GTGCTGGCAG GCCCCGGGGG TCCCGGGAAC   3180
```

```
GGGCTGCGGT CCCTGTACCC GCCCCCGCCA CCTCCGCAGC ACCTGCAGAT GCTGCCGCTG        3240

CAGCTGAGCA CCTTTGGGGA GGAGCTGGTC TCCCCGCCCG CGGACGACGA CGACGACAGC        3300

GAGAGGTTTA AGCTCCTCCA GGAGTACGTG TATGAGCACG AGCGGGAAGG GAACACCGAA        3360

GAAGACGAAC TGGAAGAGGA GGAGGAGGAC CTGCAGGCGG CCAGCAAACT GACCCCGGAT        3420

GATTCGCCTG CGCTGACGCC TCCGTCGCCT TTCCGCGACT CGGTGGCCTC GGGCAGCTCG        3480

GTGCCCAGCT CCCCAGTGTC CGAGTCGGTG CTCTGCACCC CTCCCAACGT ATCCTACGCC        3540

TCTGTCATTC TGCGGGACTA CAAGCAAAGC TCTTCCACCC TG                          3582
```

(2) INFORMATION FOR SEQ ID NO:3:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..60

(xi) SEQUENCE DESCRIPTION: SEQ ID NO:3:

```
ATGGTCGGGC TCCTTTTGTT TTTTTTCCCA GCGATCTTTT TGGAGGTGTC CCTTCTCCCC        60
```

(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..60

(xi) SEQUENCE DESCRIPTION: SEQ ID NO:4:

```
CCAGGACACC TTCTGGAAAA TCCCAACTTT AAACGAATCT GCACAGGCAA TGAAAGCTTA        60
```

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..60

(xi) SEQUENCE DESCRIPTION: SEQ ID NO:5:

```
AACGTATCCT ACGCCTCTGT CATTCTGCGG GACTACAAGC AAAGCTCTTC CACCCTGTAA        60
```